(12) United States Patent
Henzler

(10) Patent No.: US 8,211,008 B2
(45) Date of Patent: Jul. 3, 2012

(54) VIDEO ENDOSCOPE

(75) Inventor: Marc Henzler, Muehlheim an der Donau (DE)

(73) Assignee: Digital Endoscopy GmbH, Friedberg (DE)

( * ) Notice: Subject to any disclaimer, the term of this patent is extended or adjusted under 35 U.S.C. 154(b) by 427 days.

(21) Appl. No.: 12/617,265

(22) Filed: Nov. 12, 2009

(65) Prior Publication Data

US 2010/0125166 A1    May 20, 2010

(30) Foreign Application Priority Data

Nov. 17, 2008  (DE) .......................... 10 2008 057 734

(51) Int. Cl.
*A61B 1/04*   (2006.01)
*A61B 1/00*   (2006.01)

(52) U.S. Cl. ......... 600/109; 600/117; 600/118; 600/137
(58) Field of Classification Search ................... 600/109, 600/117, 118, 137
See application file for complete search history.

(56) References Cited

U.S. PATENT DOCUMENTS

| | | | | |
|---|---|---|---|---|
| 5,797,836 A | * | 8/1998 | Lucey et al. | 600/109 |
| 6,097,423 A | * | 8/2000 | Mattsson-Boze et al. | 348/65 |
| 7,037,258 B2 | * | 5/2006 | Chatenever et al. | 600/109 |
| 7,517,314 B2 | * | 4/2009 | Hoeg et al. | 600/117 |
| 2003/0114730 A1 | * | 6/2003 | Hale et al. | 600/114 |
| 2005/0027167 A1 | * | 2/2005 | Chatenever et al. | 600/173 |
| 2005/0228230 A1 | * | 10/2005 | Schara et al. | 600/171 |

FOREIGN PATENT DOCUMENTS

| | | |
|---|---|---|
| DE | 196 81 437 | 7/1998 |
| EP | 1 844 696 | 10/2007 |

OTHER PUBLICATIONS

German Pat. Appln. No. DE 10 2008 057 734.0 filed Nov. 17, 2008, Office Action, total 8 pages (complete English translation).

* cited by examiner

*Primary Examiner* — Rodney Fuller
(74) *Attorney, Agent, or Firm* — Andrew F. Young, Esq.; Lackenbach Siegel, LLP

(57) ABSTRACT

The invention is a sideways looking video endoscope which offers a rigid endoscope tube. The optical system has one prism, and an image sensor located behind the optical system, provided on the distal end of the endoscope shaft. On the proximal end of the shaft, a knurled wheel is arranged so as to rotate freely. This wheel is provided with permanent magnets that are arranged at identical angular separations, and associated with Hall sensors located on the front face of the tool holder. The angular position of the rotatable wheel can thus be detected by means of the Hall sensors together with an electronic system that evaluates the signals, and displayed on a monitor. By turning the rotating wheel, the image can be rotated, thus correcting the image position when the endoscope is rotated, such that the viewing direction corresponds to the actual position of the object.

9 Claims, 4 Drawing Sheets

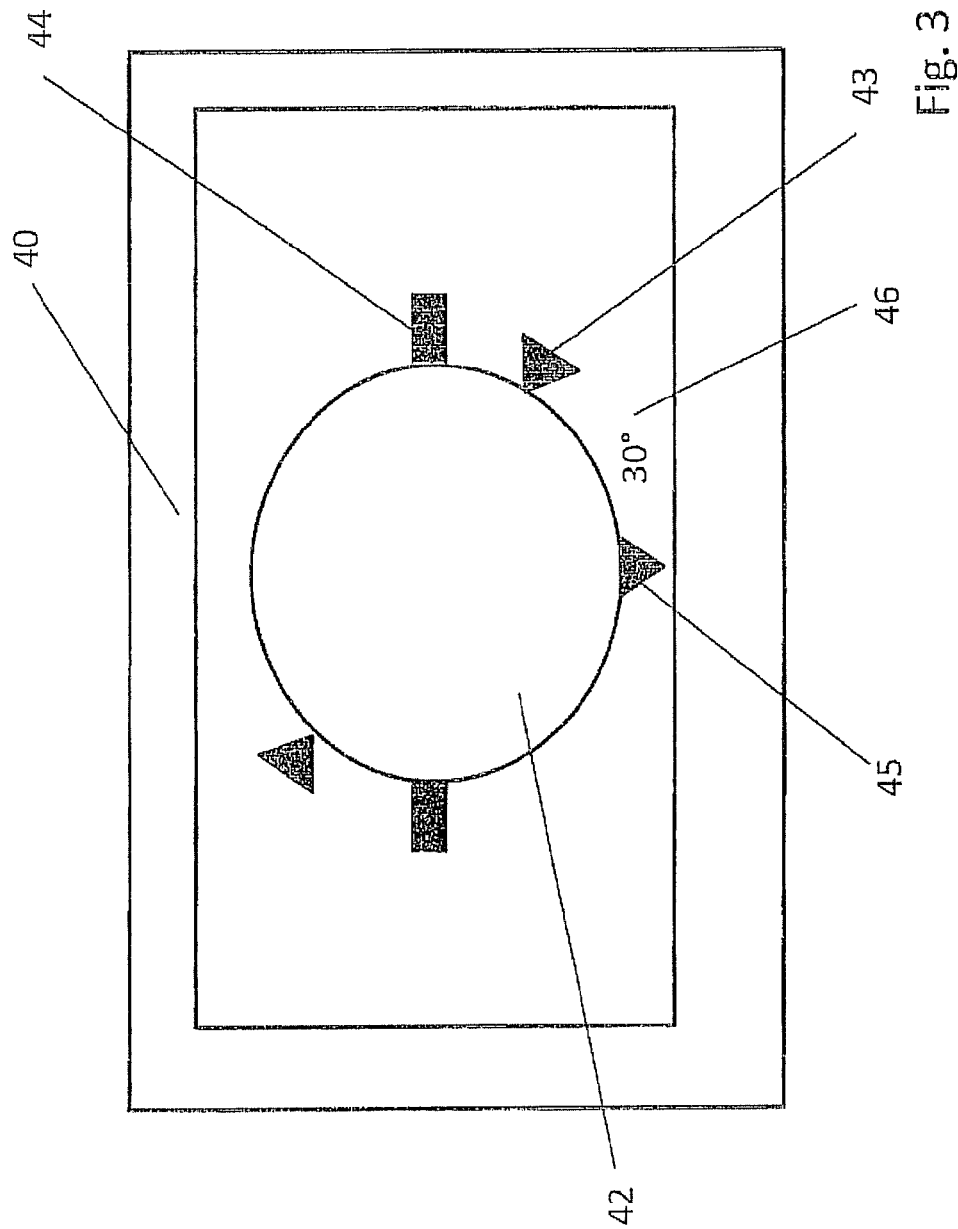

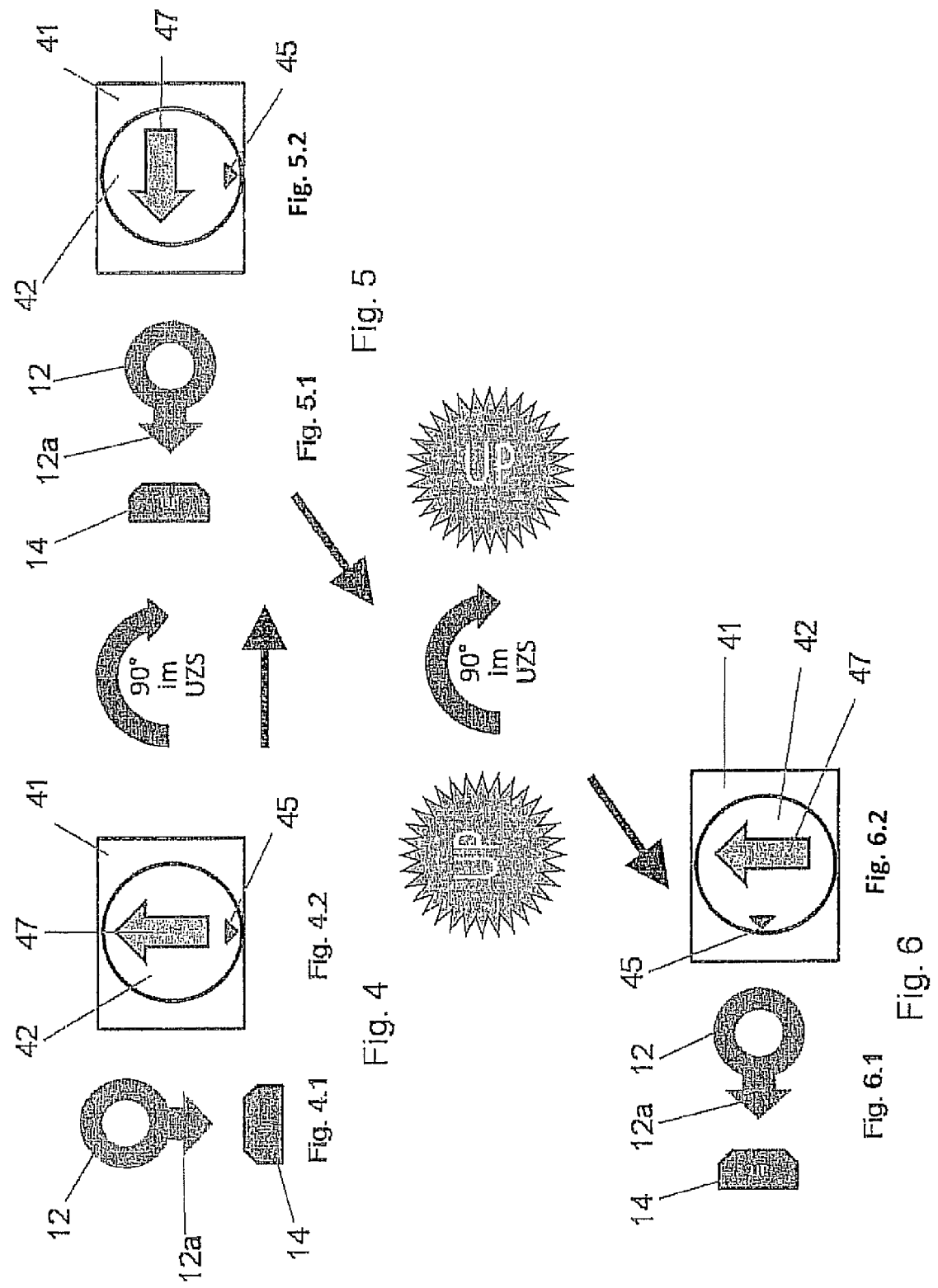

VIDEO ENDOSCOPE

CROSS REFERENCE TO RELATED APPLICATIONS

This application is related to, and claims priority from, German Patent Application Serial No. 10 2008 057 734.0, filed Nov. 17, 2008, the entire contents of which is incorporated herein by reference.

FIGURE SELECTED FOR PUBLICATION

FIG. 2

BACKGROUND OF THE INVENTION

1. Field of the Invention

The present invention relates to a video endoscope for use in diagnostic medicine, among other fields. More specifically, the present invention relates to an endoscope in which the image position can be corrected in a simple way during the rotation of the endoscope with a sideways looking optical system, and where horizontal tilting is prevented.

2. Description of the Related Art

Endoscopes, including particularly video endoscopes, allow the user to view body cavities, in a simple, minimally invasive way, for the purpose of diagnosis or also therapy. Such endoscopes are also referred to by the word technoscope or boroscope for technical applications.

In so-called rigid endoscopes, a nonflexible endoscope shaft is arranged in a tool holder, on whose distal end an optical system is provided, whose image is converted into electrical signals by an image sensor, and visualized by means of the screen of a monitor.

Such rigid endoscopes are used primarily in medicine, for example, in laparoscopy, where the optical axis of the optical system either coincides with the axis of the endoscope shaft or forms an angle of, for example, 30° or 40° with the latter. Optical systems with a viewing direction of 0° are referred to as forward looking optical systems, while angled optical systems are called sideways looking optical systems. In the case of the so-called flexible endoscopes, the tool holder with the optical system is connected via a flexible line, so that the viewing direction of the optical system can here be changed by a distal deflection of the connection hose.

In a videoscope with a non-angled optical system, i.e., a viewing direction of 0°, the object is reproduced on the screen in the position that is expected based on the position of the optical system, with a defined image horizon. The image position is here marked by an appropriate marking on the camera head or on the head of the video endoscope or by ergonomic requirements on the tool holder. The user who works with such an endoscope can thus work in front of the background of a stable image horizon, and orient himself/herself. Difficult and long-lasting adjustments by the user are not necessary.

Another situation arises during the axial rotation of an endoscope with a sideways viewing optical system, because the image position on the screen changes during the orientation, which makes it extraordinarily difficult for the user to orient himself/herself.

The reason for this is the fixed connection of the image sensor with the sideways looking optical system, which leads to the image horizon rotating on the screen during the axial rotation of the video endoscope. As a result of rotation of the image horizon, also referred to as horizontal tilting, the spatial orientation is made extraordinarily difficult for the user.

In a conventional configuration, in which the sideways looking optical system is not connected with the camera head or the image sensor, this effect, which is caused by the rotation of the sideways looking endoscope in comparison to the stable position of the camera and thus of the image sensor, does not occur. In the process, the camera head is not rotated with respect to the natural horizon; it remains in horizontal position, while only the sideways looking optical system of the endoscope is rotated. However, such a device is not easy to handle, because of the separation between the camera head and the optical system.

An additional possibility to prevent the above-mentioned horizontal tilting consists in flexibly bending the distal end of a rigid or flexible endoscope, which is provided with a forward looking optical system. As a result of the distal bending, different viewing directions can be implemented without horizontal tilting. However, the drawback here is the not inconsiderable mechanical effort, which necessarily limits the product life of such a system, which must indeed be cleaned at regular intervals by steam sterilization.

In addition, in such a system, the length of the element that is to be bent leads to a restriction of the visibility conditions in narrow cavities and body cavities, such as, for example, in the application in laparoscopy. Furthermore, bending over an angle of more than 90° with respect to the above-mentioned horizontal tilting makes it difficult for the user to orient himself/herself.

Another approach is taken with the rigid video endoscope known from German Patent No. DE 196 81 437 T1, with an endoscope shaft that is arranged on a tool holder, on whose distal end a sideways looking optical system is arranged. The image sensor, which is arranged after the optical system, is also arranged inside the endoscope shaft, but it is in its own shaft, which is located within the endoscope shaft, and can be turned with respect to the latter. By turning the image sensor shaft with respect to the endoscope shaft, an image position correction is possible, which corrects the above-mentioned horizontal tilting.

What is not appreciated by the prior art is that the two-shaft solution is particularly susceptible to breakdown, because of the shafts that have to be rotated with respect to each other, and particularly because of the required steam sterilization, leading not only to a cost increase, but also to a significantly shorter product life for such an apparatus.

Accordingly, there is a need for a video endoscope in which the image position can be corrected in a simple way during the rotation of the endoscope with a sideways looking optical system, and where horizontal tilting is prevented.

ASPECTS AND SUMMARY OF THE INVENTION

An aspect of the present invention is to provide for a video endoscope in which the image position can be corrected in a simple way during the rotation of the endoscope with a sideways looking optical system, and where horizontal tilting is prevented.

The present invention relates to a sideways looking video endoscope which offers a rigid endoscope tube. The optical system has one prism, and an image sensor located behind the optical system, provided on the distal end of the endoscope shaft. On the proximal end of the shaft, a knurled wheel is arranged so as to rotate freely. This wheel is provided with permanent magnets that are arranged at identical angular separations, and associated with Hall sensors located on the front face of the tool holder. The angular position of the rotatable wheel can thus be detected by means of the Hall sensors together with an electronic system that evaluates the signals, and displayed on a monitor. By turning the rotating wheel, the image can be rotated, thus correcting the image position when the endoscope is rotated, such that the viewing direction corresponds to the actual position of the object.

According to the fundamental idea of the invention, this problem is solved by rotating the image that has been taken by the image sensor and transferred to a screen, by electronic means for the purpose of correcting the image position.

In terms of construction, this method is solved with a video endoscope of the type mentioned in the preamble by the fact that on the proximal end of the endoscope, close to the tool holder, a rotating wheel that can be rotated freely is arranged, where the rotating wheel and the tool holder present sensors which generate signals that characterize the rotation angle of the rotating wheel with respect to the tool holder, and are then supplied via the electronic system to the monitor for the rotation of the monitor image, where the viewing direction and the viewing angle of the optical system are displayed on the screen on the monitor. In this arrangement, the rotation of the rotating wheel is acquired for the generation of the signals, where the position of the rotating wheel during the switching on of the apparatus is chosen as starting point.

Suitable sensors are Hall sensors which are arranged in the tool holder, connected to the electronic system, and associated with permanent magnets that are distributed in the rotating wheel at equal angular distance over the periphery. When the rotating wheel is rotated, the Hall sensors generate signals that characterize the rotation angle. It is advantageous to arrange twelve permanent magnets at identical angular separations in the rotating wheel, and two Hall sensors at the angular separation of 180° in the tool holder. An angular separation of 180° between the Hall sensors is here not an absolute requirement. Rather, the Hall sensors can also be arranged advantageously in such a way that, in the case of a Hall sensor position that overlaps with a permanent magnet, the other Hall sensor is located between two permanent magnets. As a result, rotation movements with a resolution of at least 7.5° can be acquired. Changes of the angles in this small range are perceived as continuous by the user.

A single-hand operation of the video endoscope, according to the invention, is made possible because the rotating wheel, in the vicinity of the tool holder, is arranged in such a way that it can be rotated by the user who is holding the tool holder with the fingers, for example, with the thumb of the same hand. Such a positioning is advantageous, because the user of conventional endoscopic cameras is used to the positioning of such adjustment means for setting the focus or changing the focal length with the so-called zoom function. As is known in itself, the peripheral surface of the rotating wheel should possess a structure that increases friction, for example, a roughening, corrugation, ribbing or the like.

An additional advantage, that is particularly pertinent to cleaning, is achieved if the rotating wheel can be removed from the endoscope shaft. This is possible, because the rotation of the rotating wheel is acquired without contact, and the tool holder is connected with hermetical seal, i.e., steam-proof, to the endoscope shaft. No expensive sealing of movable parts is required.

To improve the orientation of the user, it is proposed to insert in its margin, in a manner similar to conventional sideways looking endoscopes, the viewing direction as well as the viewing angle in the monitor image.

Finally, the proposal is made to arrange, in the way that is known from European Patent No. EP 1 844 696, at least one gravitation sensor in the tool holder, which is connected to the monitor via the electronic system to display the true image horizon. Thus, the user has the possibility of indicating the position of the true horizon after an appropriate calibration, and to rotate the image by turning the rotating wheel in such a way that the true horizon is brought into the horizontal position.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 3 shows a pictorial representation of the screen of the associated monitor; and FIGS. 4, 5, and 6 show schematic representations of the video endoscope (FIGS. 4.1, 5.1 and 6.1) with associated screen representations (FIGS. 4.2, 5.2 and 6.2).

DETAILED DESCRIPTION OF THE PREFERRED EMBODIMENTS

Figure 1:
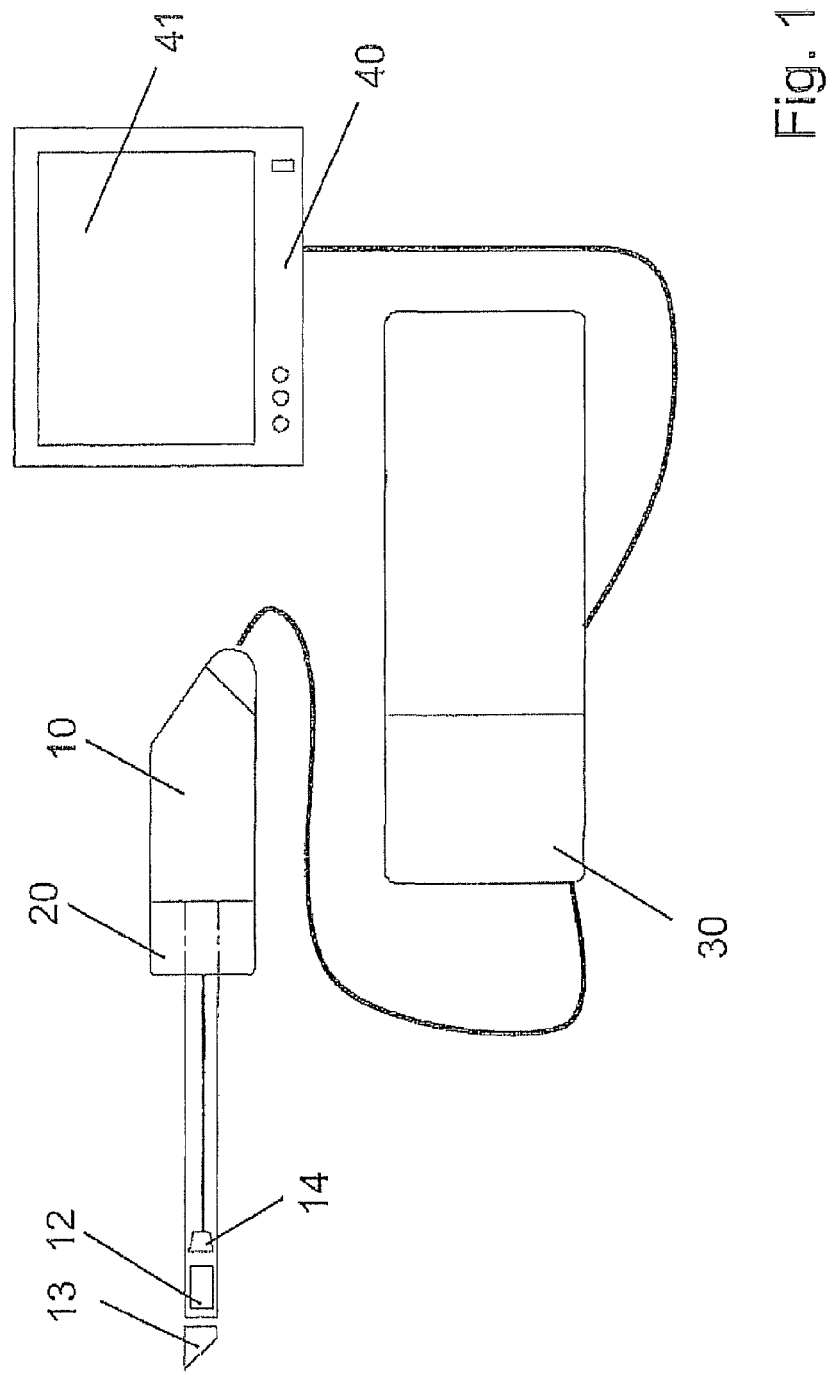
FIG. 1 shows a schematic diagram of a video endoscope according to the invention with control apparatus and monitor.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

The overall circuit for a video endoscope 10 according to the invention, which is connected via a control apparatus 30 to the monitor 40, is represented in FIG. 1.

Figure 2:
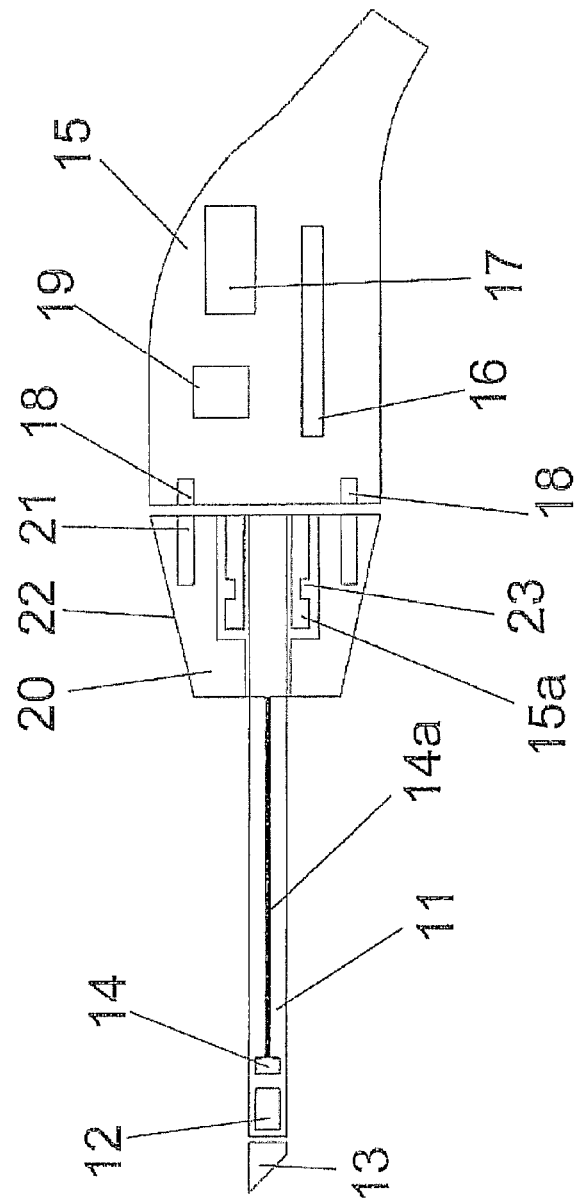
FIG. 2 shows an enlarged cross-sectional representation of the video endoscope according to the invention.

FIG. 2 shows the more precise structure of the video endoscope 10 according to the invention. It consists substantially of a tool holder 15, on whose front side the endoscope shaft 11 is arranged, which is inserted in a hermetically sealing way, particularly in a steam-proof way, in a connector 15a of the tool holder 15. The optical system 12, whose viewing direction is determined by a prism 13 arranged in front of the optical system, is located at the distal end of the endoscope shaft 11. The image generated by the optical system 12 is projected on an image sensor, also called image sensor, which is located inside the endoscope shaft 11, and which converts the recorded image into electrical signals that are supplied via a line 14a to the electronic system located in the tool holder 15. On the connector 15a of the tool holder 15, the rotating wheel 20 is arranged in a haptically advantageous position, so it can rotate freely, and, on its side facing the tool holder 15, it is fitted with 12 permanent magnets 21 arranged at identical angular separations. Two Hall sensors are arranged at an angular separation of 180° on the opposite side of the tool holder 15. By means of the Hall sensors 18 and the rotatable permanent magnets 21 opposite them, the position of the rotating wheel 20 can be detected. The signal generated by the Hall sensors 18 is supplied via an evaluation electronic system 16 through the control apparatus 30 to the monitor 40 for displaying the position of the video endoscope. The rotating wheel 20, whose surface 22 is corrugated to improve the grip, is arranged on the tool holder 15 in such a way that it can be rotated conveniently by the user using the fingers of the hand that holds the tool holder 15.

The rotating wheel 20 can be pulled off, particularly for the purpose of cleaning the endoscope shaft 11, for example, by steam sterilization.

Because the Hall sensors 18 and the permanent magnets 21 can be used to acquire without contact the rotation movement or the position of the video endoscope, there is no need for an expensive sealing of movable parts.

Furthermore, gravitation sensors 17 and a compass 19 are provided in the tool holder, by means of which, after an appropriate calibration, the position of the true horizon as well as the exact local position of the image sensor can be acquired, and reproduced on the screen 41 of the monitor 40.

Using the video endoscope 10 according to the invention, the screen image 42 illustrated in FIG. 3 can be generated via the control apparatus 30. The latter image shows the image 42 of the optical system, a marking 43 for the true horizon, and a marking 44 for the virtual horizon. Also included are, near the image margin at 45, the viewing direction, and at 46, the viewing angle of the optical system used. These displays can be adapted in accordance with the format and the resolution of the image on the screen 41.

The commonly used reproductions on the screen 41 usually employ image formats with a ratio of 5 to 4 and a resolution of 1280×1024 pixels, or a ratio of 19 to 10 with a resolution of 1920×1200 pixels.

By means of the rotating wheel according to the invention, the image 42 on the screen 41 of the monitor 40 can be rotated electronically, as explained below in reference to FIGS. 4-6.

In FIGS. 4.1, 5.1 and 6.1, the optical system is symbolized with a circle 12, and its viewing direction with an arrow 12a. The image sensor is associated in a fixed way with the optical system as far as its position is concerned, and illustrated with the symbol 14.

FIGS. 4.2, 5.2 and 6.2 schematically show the images that are represented on the screen 41, and recorded by the optical system; they are symbolized here with an arrow 47.

FIGS. 4.1 and 4.2 represent the position of the video endoscope and the corresponding representation on the monitor for the case where the viewing direction 12a of the optical system 12 points downward, and the image sensor 14 is located parallel to the true horizon. In this case, the object recorded by the optical system 12, here symbolized by the arrow 47, is reproduced in its true position in the image 42 of the optical system.

When the video endoscope is rotated 90° clockwise from the position represented in FIG. 4.1, into the position represented in FIG. 5.1, the image 42 reproduced on the screen 40 is rotated in the opposite direction, where the viewing direction 12a rotates as a result of the process exactly with the rotation of the video endoscope or more precisely with the optical system 12. Nonetheless, the display of the viewing direction 45 and also the viewing angle remain in an unchanged position on the screen 41, because the image 42 indicates the viewing direction of the optical system 12 toward the image sensor 14. This results, for the user, in the interfering horizontal tilting.

With the solution according to the invention, he has the possibility of rotating the image 47 reproduced on the screen 41 in accordance with the rotation of the video endoscope, i.e., of the optical system 12. For this purpose, the user turns the rotating wheel 20 in the same viewing direction and by the same rotation angle on the shaft of the video endoscope. As a result, the image 42 is rotated from the position represented in FIG. 5.2 into the position represented in FIG. 6.2, so that the display of the viewing direction now corresponds exactly to the actual viewing direction of the video endoscope. The horizon of the image 42 now runs parallel to the true horizon, which corrects the interfering horizontal tilting.

Corresponding courses, but in the opposite direction, are obtained when the video endoscope is rotated counterclockwise.

In the claims, means or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a, bolt may be readily understood by those skilled in the art as equivalent structures.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. A video endoscope, said video endoscope further comprising:
    an endoscope shaft that is arranged in a tool holder, wherein:
    (a) wherein, on a distal end of said tool holder a sideways looking optical system is arranged, and an image sensor which is arranged after the optical system, and connected to a monitor for image reproduction via an electronic system;
    (b) wherein, on a proximal end of said endoscope shaft, close to said tool holder, a rotating wheel that can be rotated freely is arranged, in that said rotating wheel and said tool holder have one or more sensors;
    (c) wherein said one or more sensors generate signals that characterize the rotation angle of the rotating wheel with respect to said tool holder, which signals are supplied via said electronic system to said monitor for rotating said monitor image; and
    (d) wherein the viewing direction and the viewing angle of said optical system are displayed on said screen of said monitor.

2. The video endoscope of claim 1, wherein said electronic system is located in said tool holder.

3. The video endoscope of claim 1, wherein a set of one or more permanent magnets are arranged in said rotating wheel, over the periphery of said rotating wheel and at identical angular separations, and Hall sensors that are associated with said set of one or more permanent magnets and connected to said electronic system are arranged in said tool holder.

4. The video endoscope of claim 3, wherein twelve permanent magnets in said rotating wheel at identical angular separations, and two Hall sensors, are arranged in said tool holder at an angular separation of 180°.

5. The video endoscope of claim 1, wherein said rotating wheel is arranged in the vicinity of said tool holder in such a way that it can be rotated by a user holding said tool holder with the fingers of the user's same hand.

6. The video endoscope of claim 5, wherein said rotating wheel surface possesses a structure that increases its coefficient of friction.

7. The video endoscope of claim 1, wherein said rotating wheel can be removed from said endoscope shaft.

8. The video endoscope of claim 1, wherein the viewing direction and the viewing angle are inserted in the margin of said monitor image.

9. The video endoscope of claim 1, wherein at least one gravitation sensor, which is connected for displaying the true image horizon via the electronic system to said monitor, is arranged in said tool holder.

* * * * *